United States Patent [19]

Raj

[11] 4,229,290

[45] Oct. 21, 1980

[54] COMPACT LOW SURFACE AREA DIALYZER METHOD AND APPARATUS

[76] Inventor: Ghen M. G. Raj, 38 Forestwood Dr., Stamford, Conn. 06903

[21] Appl. No.: 886,458

[22] Filed: Mar. 14, 1978

[51] Int. Cl.² .................... B01D 13/00; B01D 31/00
[52] U.S. Cl. .............................. 210/646; 210/321 B; 128/214 B
[58] Field of Search ............... 210/321 A, 321 B, 231, 210/22, 23 H, 23 F, 433 N; 128/214 R, 214 B, DIG. 3; 55/159

[56] References Cited

U.S. PATENT DOCUMENTS

| | | | |
|---|---|---|---|
| 1,757,364 | 5/1930 | Heibig | 210/321 A |
| 2,686,154 | 8/1954 | MacNeill | 210/321 B |
| 3,074,559 | 1/1963 | Savino | 210/321 B |
| 3,352,422 | 11/1967 | Heden | 210/321 R |
| 3,459,310 | 8/1969 | Edwards | 210/321 B |
| 3,464,562 | 9/1969 | Meyers et al. | 210/321 B |
| 3,523,408 | 8/1970 | Rosenberg | 55/159 |
| 3,540,595 | 11/1970 | Edwards | 210/321 B |
| 3,910,841 | 10/1975 | Esmond | 210/321 B |
| 3,932,283 | 1/1976 | Esmond | 210/321 B |

Primary Examiner—Charles N. Hart
Assistant Examiner—David R. Sapowski
Attorney, Agent, or Firm—Cooper, Dunham, Clark, Griffin & Moran

[57] ABSTRACT

A compact blood dialyzer is described having a low surface area of semi-permeable membrane as compared with the dialyzer systems in use today. The dialyzer can be manufactured at relatively low cost to be provided as a presterilized unit feasible for use in dialysis at home. Arterial pressure can pump the blood through the compact dialyzer unit. The blood and dialysate flow in multiple parallel channels on opposite sides of the semi-permeable membranes, with the blood being directed as wide thin films travelling against the surface of the membrane, thereby providing an efficient exposure of the flowing blood to the surface of the membrane. Advantageously, the blood flows upwardly in its channels against gravity for assuring complete filling of each and every channel with the blood being effectively pushed against the surface of the membrane for enhancing the osmotic action. The dialyzer unit is shown flexed into an arc during usage for clamping the plates firmly against the membrane sandwiched between them.

17 Claims, 11 Drawing Figures

COMPACT LOW SURFACE AREA DIALYZER METHOD AND APPARATUS

FIELD OF THE INVENTION

The present invention is in the field of blood dialysis and more particularly relates to method and apparatus of extracorporeal dialyzing of blood and wherein only a very small percentage of the patient's total blood volume is flowing in extracorporeal relationship through the dialyzing apparatus.

The dialyzer method and apparatus disclosed and claimed herein are also suitable for pediatric and veterinary usage.

BACKGROUND OF THE INVENTION

The background of the present invention is set forth eloquently in an article written by Martha K. Kwitny, herself a kidney patient and a Deputy Attorney General in the Antitrust Section of the New Jersey Attorney General's office, entitled: "Alternatives to Kidney Dialysis," which appeared on the editorial page of the Wall Street Journal, Mar. 1, 1978. The Kwitny article is incorporated herein by reference and a copy is attached as Exhibit "A" to this application.

Supplementing the agonizing human problems discussed in that article, as caused by prior art dialyzing systems, it is noted that a grown human has a blood volume of approximately 5,000 to 6,000 milli liters (ml–approximately 5 to 6 quarts). Some of the numerous technical problems with the large dialyzer systems as discussed in the Kwitny article in use today are as follows:

1. From approximately 300 ml to 800 ml of the patient's blood is withdrawn from the patient and flows in extracorporeal relationship through such large, bulky, expensive dialyzer systems of the prior art. In other words, from approximately 5% to 16% (or even more for a smaller person) of the patient's total blood volume is flowing outside of the patient's body, which is inherently a risky arrangement.

2. Withdrawing such a high percentage of the patient's total blood volume often leads to cramps, such as leg cramps, and can cause shock to occur in the patient.

3. If clotting should occur in the dialyzer system, then the patient must be disconnected, and immediately there is a loss of from 300 ml to 800 ml of blood, which is left clotted in the dialyzer.

4. A pump is used to circulate the extracorporeal blood under pumping pressure through such a large dialyzer system. Such pumps routinely damage or break blood cells, which is deleterious to the patient.

5. The pumping pressure (which is considerably higher than normal blood pressure) places stress on the semipermeable membrane of the prior art dialyzer system and increases the risk of membrane rupture, which occurs from time to time in such prior art dialyzer systems.

6. The large, bulky, expensive prior art dialyzer systems often have a large tank, for holding the dialysate brine solution, such as one containing 120 gallons for simultaneous use by several patients in common. It is not feasible to sterilize such a large tank of brine solution, and there are organisms called pseudomonas which can live in such extremely salty solutions. Consequently, a patient using such a prior art system is continually at risk of getting a serious pseudomonal septicemia (blood infection from pseudomonas) in event of membrane rupture allowing dialysate solution to leak into the patient's blood. These pseudomonas organisms are very difficult to kill in a septicemia because they are almost insensitive to the various known antibiotics.

7. A number of patients are all connected to the same overall dialyzer system which is an inherently risky situation.

8. The flow rate in such large prior art dialyzer systems in handling approximately 300 ml to 800 ml of blood is such that it requires about twenty minutes for this quantity of blood to pass through the system and to return to the patient's body. In other words, this means that there is about one "pass-through" of handled blood in twenty minutes, which only amounts to three pass-throughs of handled blood per hour.

9. Complex monitoring equipment is needed, including that to make certain that the pumping pressure does not become too high and to determined whenever a membrane ruptures.

10. Since the patient is connected to an expensive prior art dialyzer system at a doctor's office or at a medical service center, there is inherent time and economic pressure, which may dictate that the patient's blood must be dialyzed at a faster rate than that which is optimum for the particular patient. Various patients often have markedly different optimum dialyzing rates due to their differing conditions. Consequently, use of the prior art dialyzer systems tends to be a harshly brutal experience for many patients as reflected by Martha K. Kwitny's writing, discussed above.

It is among the objects of the present invention to overcome these problems of the prior art.

SUMMARY OF THE INVENTION

Among the numerous advantages of employing the present invention are those resulting from the fact that relatively compact dialyzer apparatus can be provided. In this compact dialyzer apparatus, the volume of extracorporeal blood is only approximately 30 ml, which is usually much less than one-tenth that handled in the prior art systems, as discussed above.

Furthermore, the patient's arterial blood pressure is usually sufficient to pump this small volume of extracorporeal blood through the compact dialyzer apparatus at a rate of approximately 120 to 170 ml per minute.

Accordingly, no pump is needed and elevated pumping pressures are avoided.

A flow rate of 120 ml to 170 ml per minute in handling only 30 ml extracorporeal blood means that approximately 4 to 5.7 "pass-throughs" of handled blood are attained per minute, which equals 240 to 340 pass-throughs of handled blood per hour.

Advantageously, a compact dialyzer embodying this invention can be provided as a pre-sterilized disposable unit and at relatively low cost. Moreover, the dialysate can be sterilized, thereby greatly reducing the chance of septicemia.

A further advantage of the dialyzer method and apparatus of the present invention is that dialysis at home can feasibly be carried out.

In the remote event that clotting or membrane rupture should occur, the patient can be disconnected from the dialyzer apparatus, thereby losing only about 30 ml of blood, which is only about ½ of one percent of the usual total blood volume of an adult.

Furthermore, in view of the relatively small extracorporeal volume of blood involved in employing the method and apparatus of this invention, it becomes convenient to perform blood dialysis where the total body blood volume is as low as approximately 1,000 ml or even lower. In other words, this compact apparatus is well adapted for blood dialysis with pediatric patients and in veterinary situations with domestic animals.

The various objects, aspects and advantages of the dialyzer method and apparatus of the present invention will become more fully understood from a consideration of the accompanying drawings in conjunction with the following detailed description of the best mode which I know for putting this invention into practice.

BRIEF DESCRIPTION OF THE DRAWINGS

FIG. 4 is an exploded plan sectional view of the dialyzer. In other words, FIG. 4 is a section similar to FIG. 3 except that the respective plates and semi-permeable membranes are shown flat and enlarged and in more detail. They are shown separated one from another to reveal the structural details of the flow channels more clearly;

DETAILED DESCRIPTION OF A PREFERRED EMBODIMENT

Figure 1:
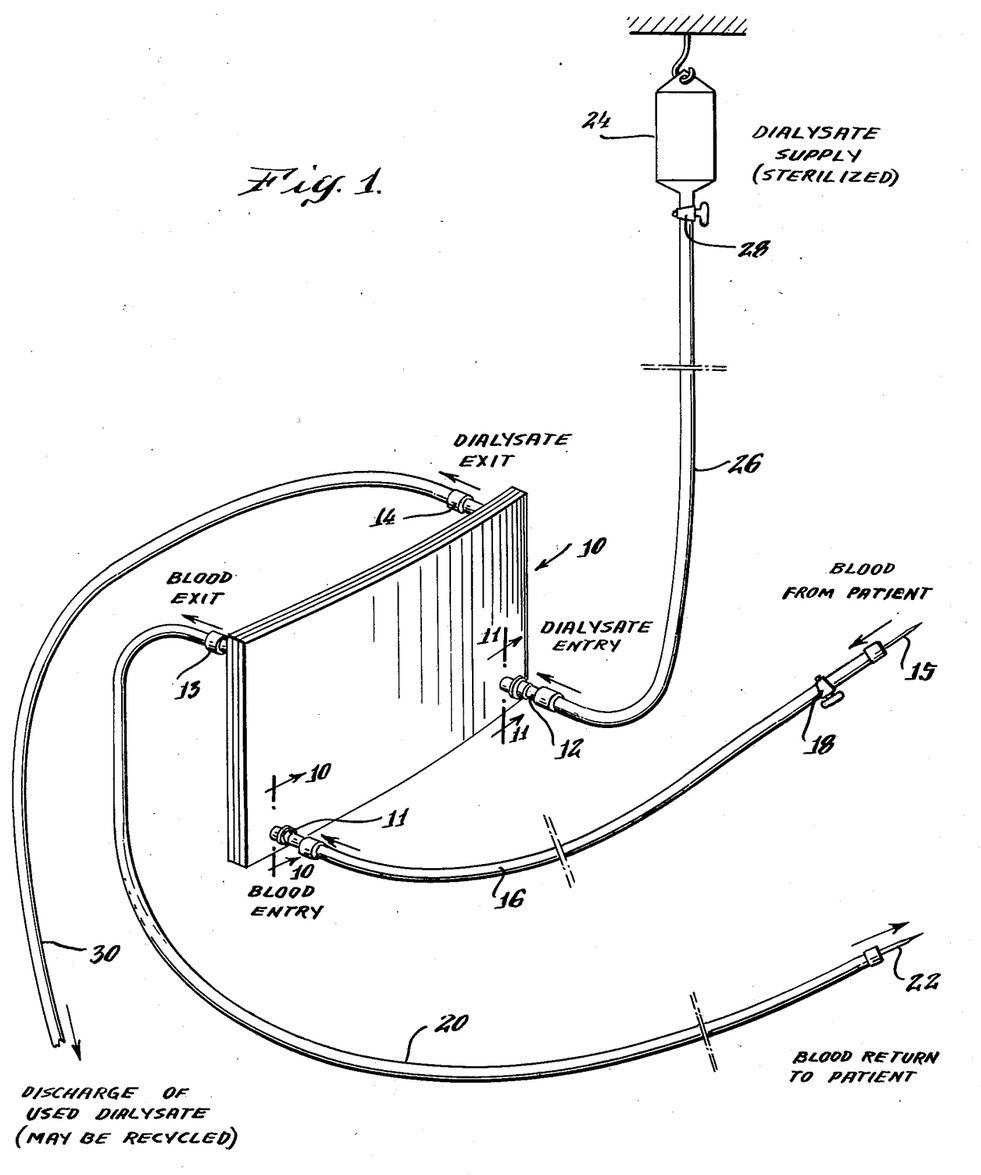
FIG. 1 is an illustration of the compact dialyzer employing the blood dialysis method of the present invention.

As shown in FIG. 1, the dialyzer 10 has four connections 11, 12, 13 and 14. The blood from the patient is fed into the dialyzer through the connection 11, while dialysate is also being fed into it through the connection 12. These respective front connections 11 and 12 are located near opposite corners near the bottom of the dialyzer 10. The blood exits through the connection 13, and dialysate exits through the connection 14 which are near opposite corners near the top rear of the dialyzer unit. All of the connections 11-14 are conveniently made through nipples as will be explained later.

The blood is obtained from an artery of the patient by inserting a hypodermic needle 15 in conventional manner and flows through a flexible tube 16 into the dialyzer. A clamp 18 may be used at any time desired to shut off the flow. The patient's blood has been treated so as to inhibit coagulation by use of a suitable anticoagulant such as heperin in a conventional procedure.

It is to be noted that the arterial pressure is usually sufficient to propel the blood during the extracorporeal flow through this compact dialysis unit 10. As will be explained, the total surface area of the semi-permeable membranes in this dialyzer unit is relatively small and thus the flow resistance for passage of blood through the dialyzer is relatively small and is predictable and reliable in value. Therefore, a mechanical pump is not needed to pump the blood through the dialyzer unit. Nevertheless, a very effective dialyzing action is obtained because the blood is directed in multiple thin films through multiple channels in which it is exposed to the membrane, as will be explained.

The return flow of dialyzed blood passes from the nipple connection 13 through a flexible tube 20 to another hypodermic needle 22 which is inserted into a vein of the patient in conventional manner.

The dialysate is supplied from an elevated container 24 and flows by gravity down through a flexible tube 26 into the dialyzer. A clamp 28 is used to adjust the flow rate, and it may be used to shut off the flow at any time. If an increase is desired in the modest pressure and flow rate at which the dialysate is supplied to the entry connection 12, then the elevation of the container 24 above the entry 12 is increased, and vice versa. It is important to note that only a relatively small overall quantity of dialysate is required for dialyzing a full grown human being. Therefore, it can readily be supplied in sterilized condition in one or more pre-filled sterilized containers 24.

The used dialysate is discharged through a flexible tube 30 and may be discarded. If the situation is such that reuse of the dialysate is appropriate, it may be passed through activated charcoal to be recycled.

The dialyzer unit in FIG. 1 is shown curved slightly into an arc. This arced condition serves to clamp the plates and membranes in the dialyzer firmly together as will be explained by reference to FIGS. 2–4.

The compact dialyzer 10 includes first, second and third rectangular plates 31, 32 and 33 (FIG. 4) which are stiffly flexible, for example made of suitable plastic material, such as polycarbonate. There are first and second semi-permeable rectangular membranes 34 and 35 sandwiched respectively between the first and second pair of plates and between the second and third plates, which form another pair. These semi-permeable membranes 34 and 35 are made of the same material as conventionally used in prior art blood dialyzer systems. A suitable semi-permeable membrane material is commercially available under the trademark CUPROPHAN, made by Enka Glanzstoff, A.G., in Wuppertal, West Germany, and can be obtained in the United States from the address: Enka Glanzstoff, A.G., Executive Plaza, Archdale Drive, Charlotte, N.C. 28210.

Figure 2:
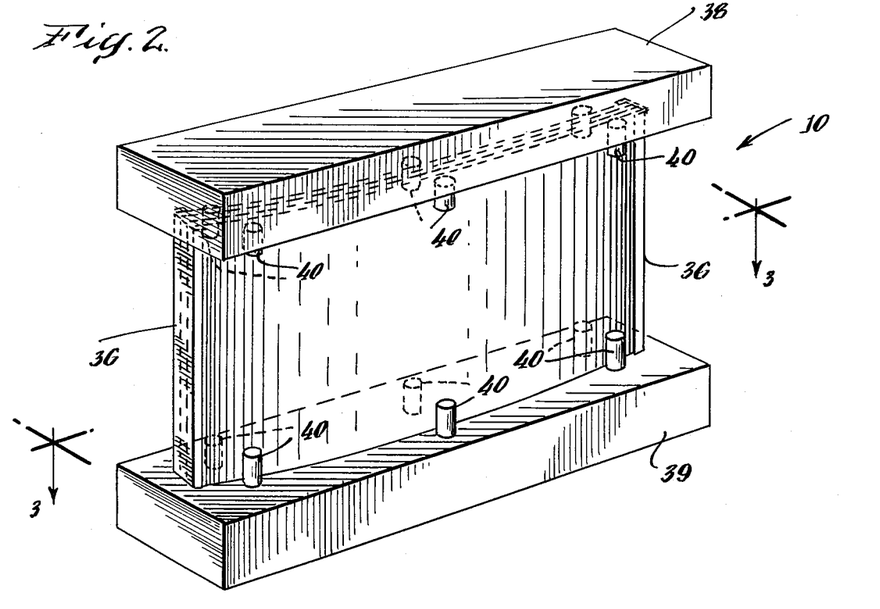
FIG. 2 is a perspective view, on a scale of approximately one-half of full size, of a compact dialyzer embodying this invention.
Figure 3:
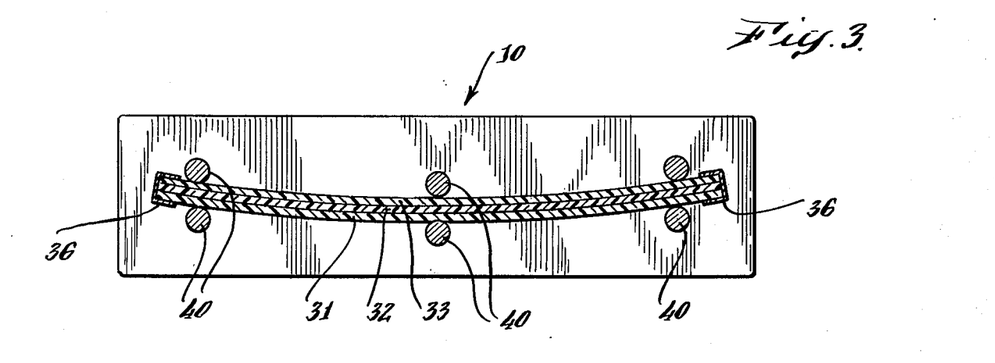
FIG. 3 is a plan sectional view of the dialyzer taken along the line 3—3 in FIG. 2.

Before assembly, the plates 31, 32 and 33 and the membranes 34 and 35 are sterilized. Then they are sealed together along all four edges by suitable edge bonding 36 (FIGS. 2 and 3). This bonding of the margins of the three plates 31, 32 and 33 can be accomplished by encapsulating the entire unit or merely encapsulating the perimeter of the unit, or by adhesively bonding the margins of the three plates together, or by ultrasonically welding them together, or the like, so as to obtain an hermetically sealed unit.

In use, the dialyzer unit is slightly bent into a gentle arc and is held in its arced condition by upper and lower clamping blocks 38 and 39 each having three pairs of projecting dowel pins 40. As seen in FIG. 3, the center pair of dowel pins 40 in each clamp block 38 or 39 are laterally offset from the other pairs for defining the arc shape for the dialyzer unit 10.

Figure 5:
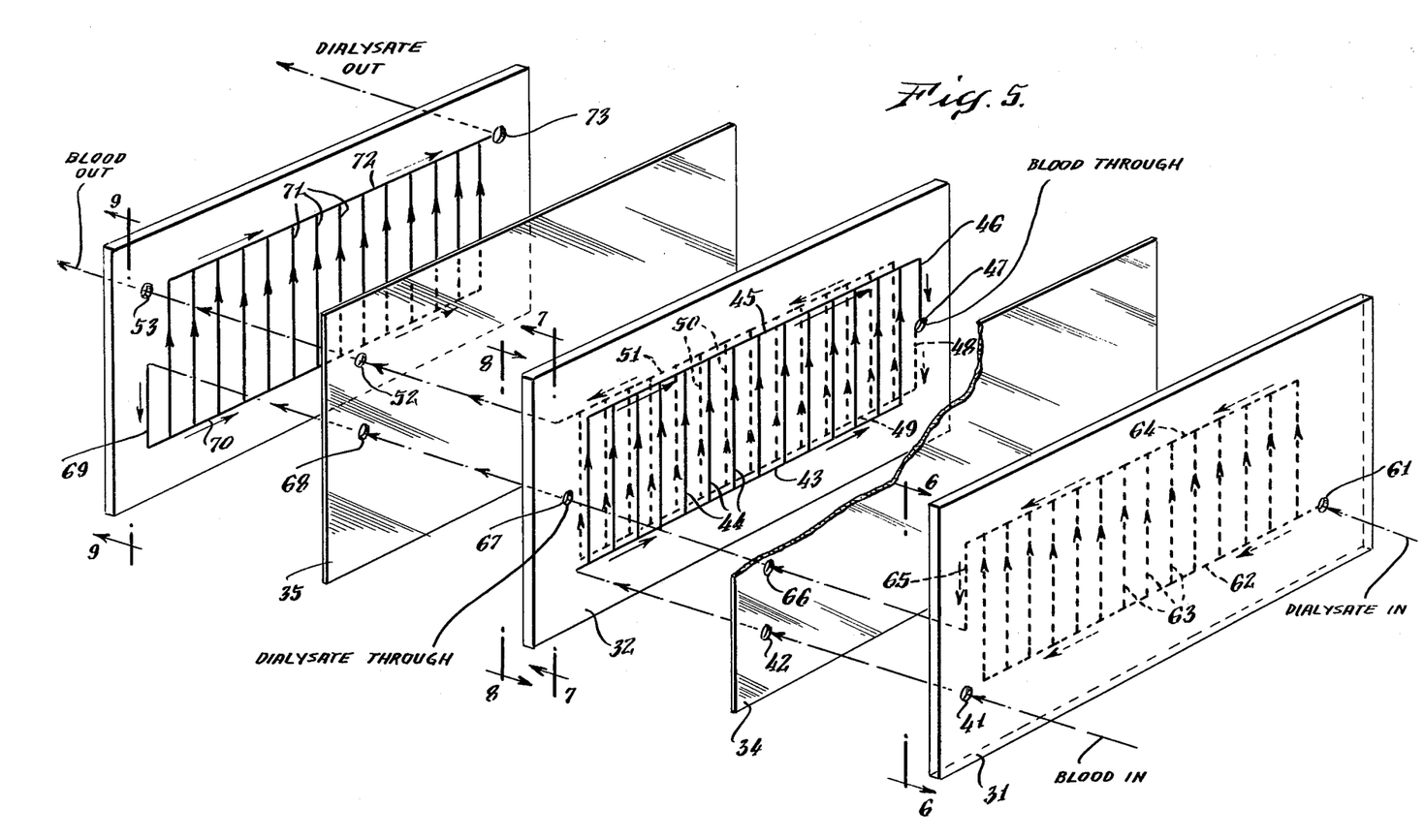
FIG. 5 is an exploded perspective view of the dialyzer with the respective plates and membranes being shown separated one from another for illustrating the flow paths of the blood and dialysate.

As seen in FIG. 5, the blood flow moves through multiple parallel channels in both the front and back of the second plate 32 (which is the center plate in this embodiment and may be considered the "blood plate"). Conversely, the dialysate flows through multiple parallel channels in the inside surfaces of the first and third plates 31 and 33.

In FIG. 5, the flow paths are shown by lines and arrows for clarity of explanation. It will be understood that the actual configuration of the flow channels and header passageways to be described can be seen in FIGS. 4 and 6 through 11.

Figure 4:
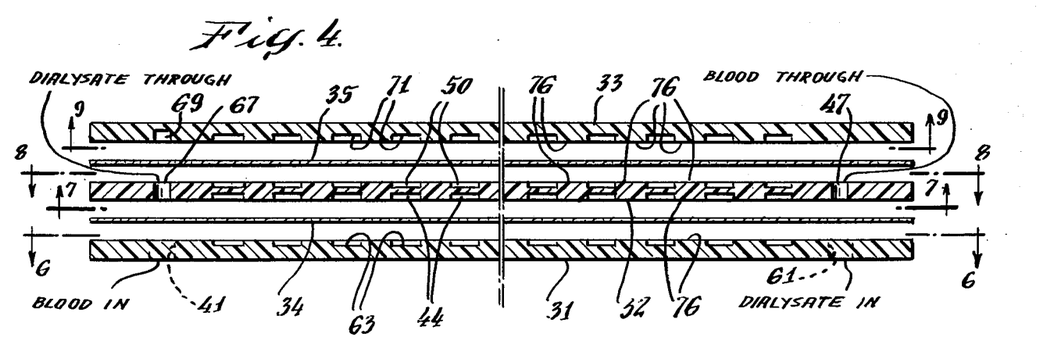

The blood enters through the nipple connection 11 (FIG. 1) and passes through ports 41 and 42 in the first plate 31 and in the membrane 34, respectively, and enters a header passageway 43 extending horizontally near the bottom edge of the second plate 32. This header passageway 43 is formed by a groove in the surface of the plate 32 as will be explained later. The blood flow moves along this header passageway 43 and is separated into multiple thin-film streams travelling upwardly through multiple channels 44 which connect into a second header passageway 45 formed by a groove extending horizontally near the top edge of the plate 32. As seen in FIG. 4, the channels 44 are adjacent to the semi-permeable membrane 34 for dialyzing the blood passing through these channels. These channels 44 are relatively shallow in the direction perpendicular to the membrane 34 so that, in effect, a relatively thin film or thin layer of blood is thoroughly and predictably exposed to the membrane.

It is to be noted that the blood flow is advantageously vertically upward through the multiple parallel channels 44, thereby flowing against gravity. In this way, the blood flow is assured of filling each and every channel 44 and of being held by gravity in intimate contact at all points with the membrane. The header passageway grooves 43 and 45 also expose the flowing blood to the membrane.

The blood which has been dialyzed in travelling in parallel flow relationship through the channel 44 becomes turbulently re-mixed in the header passageway 45 so that a uniform blood constituency is obtained before the occurrence of a second dialysis flow as will be explained.

From the end of the header passageway 45 there is a downwardly extending leg or passageway 46 which enters a port 47. The blood flows half-way down through this vertical passageway 46, passes through the port 47, then flows down the remaining half-way through a similar vertical passageway 48 (shown by a dashed line) in the back surface of the second plate 32. The downward flow passageway or leg 48 connects with an end of a third header passageway in the rear surface of the plate 32. Thus, the blood passes along this third header passageway 49 which extends horizontally along the rear of plate 32 near the bottom edge of this plate. It is positioned in alignment with the first header passageway 43 on the front surface of the plate.

Again, the blood flow is separated into multiple thin-film streams 50 travelling vertically upwardly against gravity through multiple channels 50. As seen in FIG. 4, the channels 50 are identical to the channels 44 and as seen in FIG. 5, they connect into a fourth header passageway 51 extending horizontally along the rear of the plate 32 near the top edge of this plate. In flowing upwardly through the channels 50, the blood which was previously re-mixed into a uniform constituency by turbulent flow in the passages 45, 46, 47, 48 and 49 is now subjected to a second dialysis.

The fourth header passageway 51 is aligned with the second header passageway 45 on the front surface of the plate 32, and at its end communicates with ports 52 and 53 in the membrane 35 and third plate 33, respectively. Thus, the blood exits from the port 53 through the nipple connection 13 (FIG. 1).

As seen in FIG. 5, the sterilized dialysate enters a port 61 from the nipple connection 12 (FIG. 1), and passes through the first plate 31 into one end of a first header passageway 62. This header passageway 62 is formed by a groove in the rear surface of the plate 31. The dialysate flows along this header passageway 62 and travels upwardly through multiple channels 63 which connect into a second header passageway 64 formed by a groove extending horizontally near the top edge of this first plate. As seen in FIG. 4, the dialysate channels 63 are adjacent to the semi-permeable membrane 43 and are aligned with the opposing blood channels 44 for dialyzing the blood passing through these latter channels. The dialysate channels 63 are less shallow in the direction perpendicular to the membrane 34 than the blood channels 44, so that a larger quantity of dialysate is exposed to the membrane than the thin film of blood in the channels 44.

The dialysate flow is advantageously vertically upward against gravity through the multiple parallel channels 63, thereby assuring the filling of each and every channel 63 by dialysate in intimate contact at all points with the membrane.

From the end of the second header passageway 64 there is a downwardly extending leg or passageway 65 which communicates with a port 66 in the first membrane 34 and with ports 67 and 68 in plate 32 and membrane 35, respectively. The dialysate flows half-way down through this vertical passageway 65, passes in sequence through the ports 66, 67 and 68, and then it flows down the remaining half-way through a similar vertical passageway 69 in the inside surface of the third plate 33. This downward flow passageway or leg 69 connects with an end of a third header passageway 70 in the inside surface of the plate 33. Thus, the dialysate passes along this third header passageway 70 which extends horizontally along the plate 33 near its bottom edge. It is positioned in opposition to and in alignment with the third blood header passageway 49 on the rear surface of the second plate 32.

The dialysate flow is separated into multiple streams travelling vertically upwardly against gravity through multiple channels 71. As seen in FIG. 4, the channels 71 are identical to the dialysate channels 63 in the first plate 31. As shown in FIG. 5, the channels 71 connect into a fourth header passageway 72 extending horizontally along the inside of the plate 33 near its top edge. In flowing upwardly through channels 71, the dialysate is exposed to the opposite surface of the second membrane 35 from the blood in the channels 50, the respective dialysate and blood channels 71 and 50 (FIG. 4) being aligned with each other.

The dialysate channels 71 communicate with a fourth header passageway 72 connecting with an outlet port 73 (FIG. 5) communicating with the outlet nipple connection 14 (FIG. 1).

Figures 10, 11:
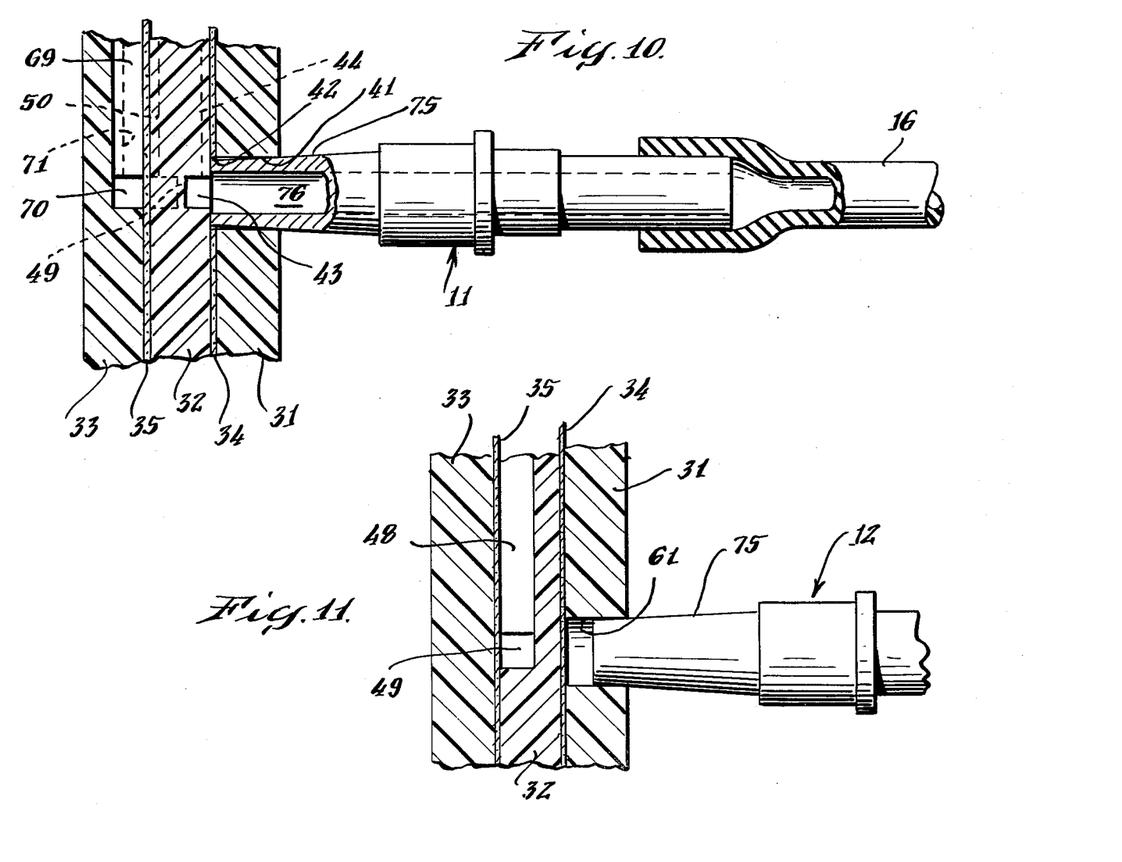
FIG. 10 is a greatly enlarged partial sectional view of the nippled connection for feeding blood into the dialyzer.
FIG. 11 is a view similar to FIG. 10 of the nipple connection for feeding dialyzate into the dialyzer.

Inviting attention to FIGS. 10 and 11, it is seen that each of the four nipples has a tapered nose 75 for tightly fitting into its respective port. In FIG. 10 the nose 75 of the blood entry nipple 11 is shown protruding inward completely through the port 42 in the first membrane 34 for assuring that the blood in the bore 76 enters the end of the first header passageway 43 on the inside (rear) surface of this first membrane 34. It is to be noted that a similar relationship exists between the inserted nose of the blood exit nipple 13 (FIG. 1) and the ports 53 and 52 so that the bore of the nipple 13 communicates with the end of the fourth header passageway 51.

As seen in FIG. 10, the header passageways 43 and 49 are deeper than the parallel flow blood channels 44 and 50. Also, the downward flow or leg passage 69 is the same depth as the header passage 70 to which it connects. This condition obtains that all four of the downward flow passages 46, 48 and 65, 69 are the same depth as the header passageway to which they connect.

FIG. 11 shows the nose of the dialysate entry nipple 12 fitting tightly into the entry port 71. It is to be understood that the dialysate exit nipple is similar to the nipple 14.

Because the blood flow channels 44 and 50 are shallower than the dialysate channels 63 and 71, it is advantageous to arrange for the blood channels to occupy both sides of the second (or central) plate 32. However, it is to be understood that this flow arrangement as shown in FIG. 5 could be relatively inverted such that the dialysate would flow through channels on opposite sides of this second plate.

Figure 7:
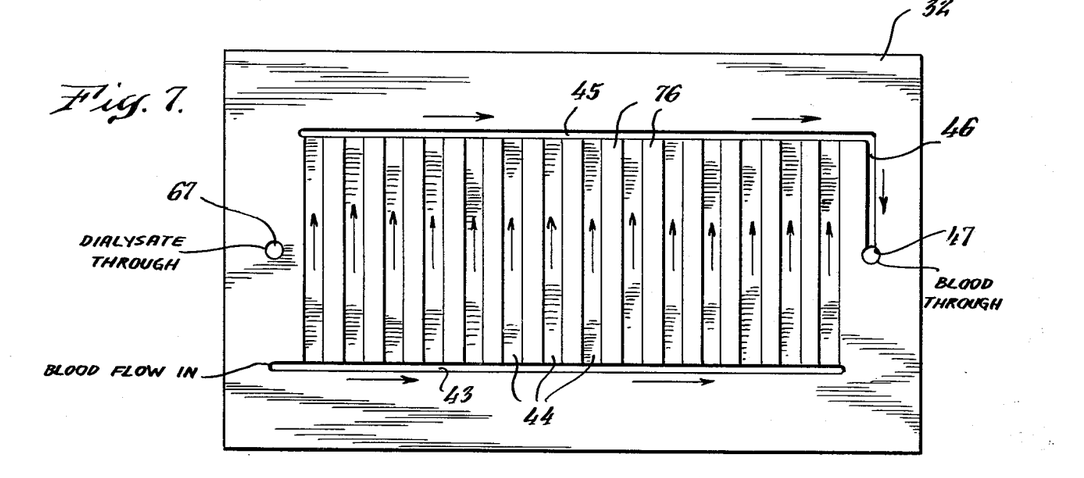
FIG. 7 is an elevational view of the front surface of the second plate as seen looking in the direction 7—7 in FIGS. 4 and 5.
Figure 8:
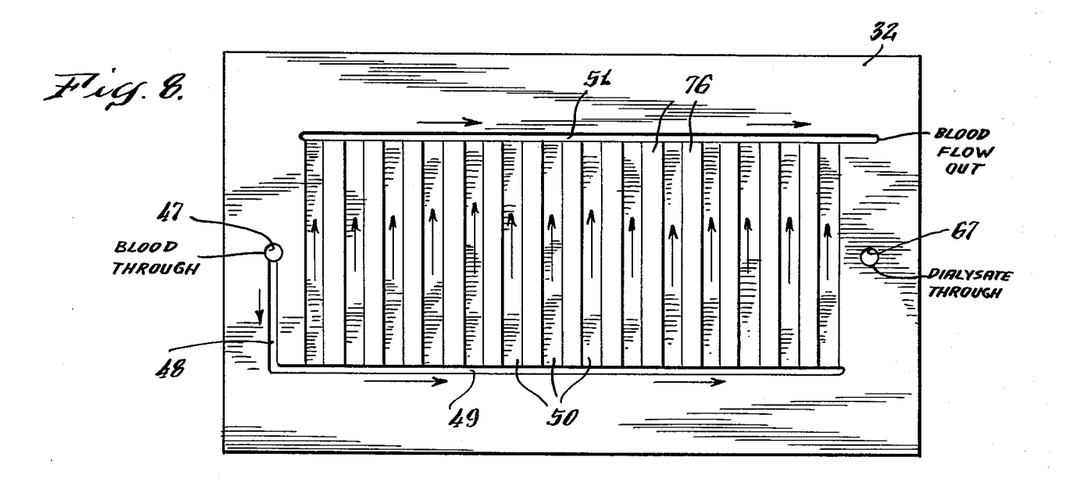
FIG. 8 is an elevational view of the rear surface of the second plate as seen looking in the direction 8—8 in FIGS. 4 and 5.
Figure 9:
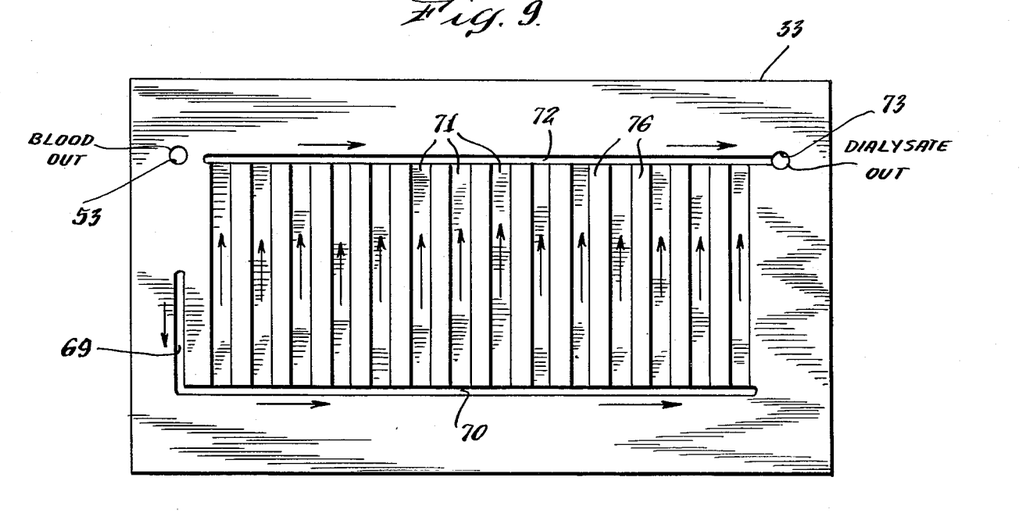
FIG. 9 is an elevational view of the inside surface of the third plate as seen looking in the direction 9—9 in FIGS. 4 and 5.

In this example as shown, the three rectangular plates 31, 32 and 33 are 4 inches high and 7 inches long. The parallel blood flow channels have a width of 0.20 inch and a depth of only 0.010 inch. Thus, their width to depth ratio is twenty, and they have a cross-sectional area of 0.002 square inch. There are fourteen blood flow channels (FIGS. 7 and 8) shown on each side of the second (or center) plate 32. It is to be noted that the pattern of blood flow passages and header passages on opposite sides of this second plate are identical, but they are oriented in different positions. This identity in pattern can be observed by comparing FIGS. 7 and 8, and by imagining that FIG. 7 is rotated through an angle of 180° with respect to the position as shown.

Figure 6:
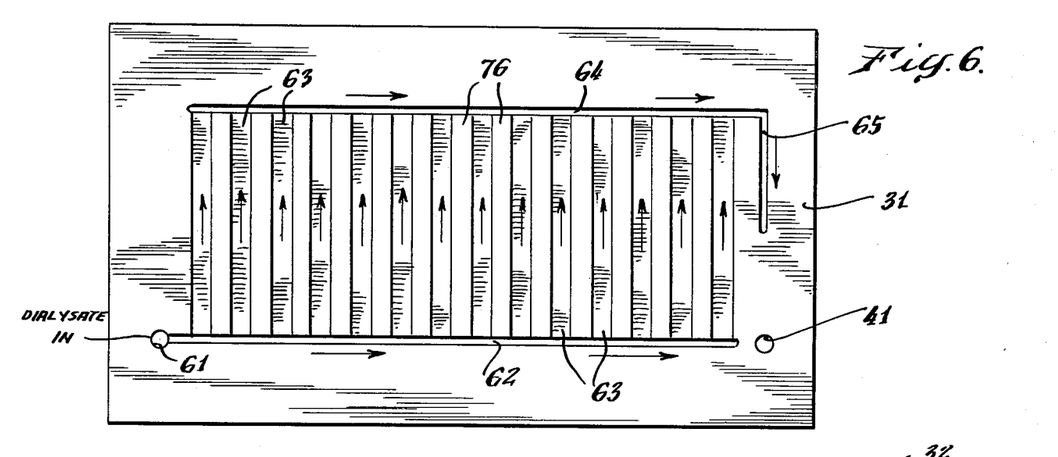
FIG. 6 is an elevational view of the inside surface of the first plate as seen looking in the direction 6—6 in FIGS. 4 and 5.

The dialysate flow channels have a width of 0.20 inch, and being three times as deep as the blood flow channels have a depth of 0.030 inch, thus providing a cross-sectional area of 0.006 square inch. The ratio of width to depth of these dialysate channels is six and two-thirds. There are fourteen of them formed on both the first and third plates 31 and 33. It is seen that the pattern of dialysate flow and header passageways is identical in the first and third plates. This identity of dialysate flow pattern can be seen by comparing FIGS. 6 and 9 and by imagining that FIG. 6 is rotated 180° from the position, as shown.

All of the header passageways have a width of 0.08 inch and a depth of 0.05 inch, thereby providing a cross-sectional area 0.004 square inch.

It was discussed in the introduction that a blood flow rate of 120 to 170 ml produces 240 to 340 "pass-throughs" of handled blood per hour. This means that different relatively small specimens of the patients blood are being subjected to dialyzing action in relatively rapid succession. Such action is somewhat analogous to a human kidney in which small specimens of the blood pass through successively. Moreover, each specimen of blood is passed through multiple wide and thin flow channels in the dialyzer unit thereby producing multiple thin films or thin layers travelling upwardly against gravity. After this first dialysis, the specimen of blood is re-mixed (in passages 45, 46, 47, 48, 49) and then is subjected to a second dialysis in sequence with the first before the blood exits from the dialyzer. It is my observation that this method of dialysis is effective.

If desired for special cases, it is possible to connect two of the compact dialyzer units 10 in series so that the blood enters the second one after it exits from the first. In such a case, there would be a second sterilized dialysate supply feeding into the second dialyzer unit.

In operation, the pressure of the dialysate within the dialyzer unit 10 is kept lower than the blood pressure in this unit. Thus, in the remote event of rupture of a semipermeable membrane, the blood enters the dialysate and almost immediately can be observed by discoloration of the discharged dialysate in the transparent flexible tube 30. It is to be noted in FIGS. 4 and 6 through 9 that the unchanneled regions or lands 76 between the respective channels 44, 50, 63, 71 are of approximately the same width as the channels thereby providing multiple supports for the membrane clamped between the plates and consequently reducing the occasion for rupture of the membrane. In other words, there are no large unsupported areas of the membrane which could produce sagging and stress concentrations. The regions of support 76 are regularly spaced for providing predictable support action for each membrane.

I claim:

1. A compact, low surface area dialyzer for extracorporeal dialysis of blood comprising:

a semi-permeable membrane suitable for blood dialysis, first and second plates positioned against opposite surfaces of said membrane and holding said membrane in sandwiched relationship between said plates, each of said plates having a multiplicity of spaced parallel flow channels formed therein on the side thereof adjacent to the respective surfaces of said membrane, said first plate having first and second header passageways formed therein, said first header passageway interconnecting one end of all of said flow channels in said first plate, said second header passageway interconnecting the other ends of all of said flow channels in said first plate, said flow channels in said first plate having a width facing said memberane and having a depth in a direction perpendicular to said membrane, said flow channels in said first plate having a width-to-depth ratio of approximately seven, first and second connection means connected to said first and second header passageways, respectively, for feeding a flow of dialysate into said first header passageway and out of said second header passageway, respectively, for flowing the dialysate through said multiple flow channels in said first plate in parallel flow relationship adjacent to one surface of said membrane, said second plate having third and fourth header passageways therein, said third header passageway interconnecting one end of all of said flow channels in said second plate, said fourth header passageway interconnecting the other ends of all of said flow channels in said second plate, the flow channels in said second plate being aligned with the flow channels in said first plate and being on the opposite side of said membrane from the flow channels in said first plate, said third and fourth connection means connected to said third and fourth header passageways, for feeding a flow of blood to be dialyzed into said third header passageway and out of said fourth header passageway, respectively, for flowing the blood through said multiple flow channels in the second plate in parallel flow relationship adjacent to the opposite surface of said membrane from the dialysate for dialyzing the blood, and the flow channels in said second plate having a depth in the direction perpendicular to said membrane and having a width facing said membrane, said flow channels in said second plate having a width-to-depth ratio of approximately twenty for exposing multiple thin wide films of flowing blood to the membrane for providing efficient exposure of the flowing blood to the surface of the membrane.

2. A compact, low surface area dialyzer for extracorporeal dialysis of blood as claimed in claim 1, in which: the flow channels for blood in said second plate are more shallow than the flow channels for dialysate in said first plate for holding a smaller volume of blood than dialysate within the unit.

3. A compact, low surface area dialyzer for extracorporeal dialysis of blood as claimed in claim 2, in which the flow channels for blood are approximately one-third as deep as those for dialysate.

4. A compact, low surface area dialyzer for extracorporeal dialysis of blood as claimed in claim 1, in which: the flow channels for blood have a depth of approximately 0.010 of an inch.

5. A compact, low surface area dialyzer for extracorporeal dialysis of blood as claimed in claim 1, in which: the flow channels for blood have a width of approximately 0.20 of an inch.

6. A compact, low surface are a dialyzer for extracorporeal dialysis of blood as claimed in claim 1, in which:
mounting means are provided for holding said first and second plates upright in vertical planes,
said flow channels for dialysate in said first plate extend vertically, and the dialysate flow therethrough is vertically upward against gravity, and
said flow channels for blood in said second plate extend vertically, and the blood flow therethrough is vertically upward against gravity,
whereby the dialysate and blood flows are assured of filling each and every channel and of being held by gravity in intimate contact with the membrane at all points along each flow channel.

7. A compact, low surface area dialyzer for extracorporeal dialysis of blood as claimed in claim 1, in which:
said plates provide multiple regions of support engaging both sides of the membrane, each of said support regions being located between each of the respective parallel flow channels.

8. A compact, low surface area dialyzer for extracorporeal dialysis of blood as claimed in claim 7, in which:
clamp means are provided for bending said first and second plates of said dialyzer into a gentle arc for pressing the plates firmly against both sides of the membrane.

9. A compact, low surface area dialyzer for extracorporeal dialysis of blood comprising:
two semi-permeable membranes suitable for blood dialysis,
first, second and third plates positioned against opposite surfaces of said membranes and holding one of said membranes in sandwiched relationship between said first and second plates and the other of said membranes between said second and third plates,
each of said plates having a multiplicity of spaced parallel flow channels formed therein on the side thereof adjacent to the respective surface of the adjacent membrane, the flow channels on opposite sides of each membrane being opposed to each other and in aligned relationship,
said flow channels in each of said plates having a relatively large width facing said membranes,
said first plate having first and second header passageways formed therein,
said first header passageway interconnecting one end of all of said flow channels in said first plate,
said second header passageway interconnecting the other ends of all of said flow channels in said first plate,
said third plate having third and fourth header passageways formed therein,
said third header passageway interconnecting one end of all of said flow channels in said third plate,
said fourth header passageway interconnecting the other ends of all of said flow channels in said third plate,
said second header passageway being connected to said third header passageway,
first and second connection means connected to said first and fourth header passageways, respectively, for feeding a flow of dialysate into said first header passageway and out of said fourth header passageway, respectively, for flowing the dialysate through said multiple flow channels in said first and third plates in parallel flow relationship adjacent to one surface of each of said membranes,
said second plate having fifth and sixth, seventh and eighth header passageways therein,
said fifth and seventh header passageways interconnecting one end of all of said flow channels on the respective sides of said second plate,
said sixth and eighth passageways interconnecting the other end of all of said flow channels on the respective sides of said second plate, with said fifth and sixth header passageways being on the same side of the second plate and said seventh and eighth header passageways being on the other side thereof,
said sixth header passageway being connected to said seventh header passageway,
third and fourth connection means connected to said fifth and eighth header passageways, for feeding a flow of blood to be dialyzed into said fifth header passageway and out of said eighth header passageway, respectively, for flowing the blood through said multiple flow channels in both sides of the second plate in parallel flow relationship adjacent to the opposite surface of each of said membranes from the dialysate for dialyzing the blood, and the flow channels in said second plate having a depth of approximately 0.01 of an inch in the direction perpendicular to said membrane and having a large width-to-depth ratio facing said membrane of approximately 20 for exposing multiple thin wide films of flowing blood to the membranes for providing efficient exposure of the flowing blood to the surfaces of the membranes said flow channels in said first plate having a width-to-depth ratio of seven.

10. A compact, low surface area dialyzer for extracorporeal dialysis of blood as claimed in claim 9, in which:

said second and third header passageways are connected to each other by a passage leading through both of said membranes and through the second plate.

11. A compact, low surface area dialyzer for extracorporeal dialysis of blood as claimed in claim 9, in which:

said sixth and seventh header passageways are connected together by a passage extending through said second plate.

12. A compact, low surface area dialyzer for extracorporeal dialysis of blood as claimed in claim 9, in which:

mounting means are provided for holding said first, second and third plates vertically oriented, and said multiple flow channels for blood in both sides of said second plate extend upward, and the blood flow therethrough is upward against gravity, whereby said upward flow of blood against gravity assures the filling of each and every channel and assures that the blood is held in intimate contact with the adjacent surfaces of the membranes.

13. A compact, low surface area dialyzer for extracorporeal dialysis of blood as claimed in claim 9, in which:

said plates provide regions of support engaging both sides of each membrane between each of the respective flow channels.

14. A compact, low surface area dialyzer for extracorporeal dialysis of blood as claimed in claim 9, in which:

the total volume of blood in said dialyzer is no more than 30 milliliters, whereby the amount of blood in said dialyzer is no more than approximately one-half of one percent of the usual total blood volume of an adult.

15. The method of extracorporeal dialysis of blood comprising the steps of:

flowing sterilized dialysate through multiple flow channels travelling adjacent to one surface of each of two semi-permeable membranes suitable for blood dialysis, the flow channels adjacent to one of said membranes having a width-to-depth ratio of seven, and those of said flow channels adjacent to the other said membrane having a width-to-depth ratio of twenty, flowing blood from a person's artery, propelling the flowing blood solely by arterial pressure, separating the flowing blood into multiple parallel flow channels travelling adjacent to the other surface of one of the semi-permeable membranes, said blood flowing in a thin film in each of said flow channels, each such thin film of blood having a thickness of approximately 0.01 of an inch, and said multiple thin films of blood on one side of the membrane being aligned with the channeled flow of dialysate on the other side thereof for producing a first dialysis of the multiple thin films of flowing blood, recombining and mixing the dialyzed blood after it has flowed in said multiple thin films, again separating the flowing blood into multiple parallel flow channels travelling adjacent to the other surface of the second of said membranes, said blood again flowing in a thin film in each of said latter flow channels, each such latter thin film of blood again having a thickness of approximately 0.01 of an inch, and said latter multiple thin films of blood on one side of said second membrane being aligned with the channeled flow of dialysate on the other side thereof for producing a second dialysis of the multiple thin films of flowing blood in sequence after the first dialysis, again recombining and mixing the blood after said second dialysis, and returning the dialyzed blood to a vein of the person.

16. The method of extracorporeal dialysis of blood as claimed in claim 15, in which:

said blood flows upwardly against gravity as it travels in said multiple thin films adjacent to the surface of the membrane, and it is propelled by the arterial blood pressure of the person whose blood is being dialyzed, and the total volume of extracorporeal blood is only a small percentage of the person's total blood volume.

17. A compact, low surface area dialyser for extracoporeal dialysis of blood comprising:

two semi-permeable membranes suitable for blood dialysis, first, second and third plates positioned against opposite surfaces of said membranes and holding one of said membranes in sandwiched relationship between said first and second plates and the other of said membranes between said second and third plates.

each of said plates having a multiplicity of spaced parallel flow channels formed therein on the side thereof adjacent to the respective surface of the adjacent membrane, the flow channels on opposite sides of each membrane being opposed to each other and in aligned relationship, said plates providing regions of support engaging both sides of each membrane between the respective flow channels and clamp means slightly bending said dialyzer into a gentle arc for clamping said plates firmly against both sides of each membrane, said flow channels in each of said plates having a relatively large width facing said membranes, said first plate having first and second header passageways formed therein said first header passageway interconnecting one end of all of said flow channels in said first plate, said second header passageway interconnecting the other ends of all of said flow channels in said first plate, said third plate having third and fourth header passageways formed therein, said third header passageway interconnecting one end of all of said flow channels in said third plate, said fourth header passageway interconnecting the other ends of all of said flow channels in said third plate, said second header passageway being connected to said third header passageway, first and second connection means connected to said first and fourth header passageways, respectively, for feeding a flow of dialysate into said first header passageway and out of said fourth header passageway, respectively, for flowing the dialysate through said multiple flow channels in said first and third plates in parallel flow relationship adjacent to one surface of each of said membranes, said second plate having fifth and sixth, seventh and eighth header passageways therein, said fifth and seventh header passageways interconnecting one end of all of said flow channels on the respective sides of said second plate, said sixth and eighth passageways interconnecting the other end of all of said flow channels on the respective sides of said second plate, with said fifth and sixth header passageways being on the same side of the second plate and said seventh and eighth header passageways being on the other side thereof.

said sixth header passageway being connected to said seventh header passageway, third and fourth connection means connected to said fifth and eighth header passageways, for feeding a flow of blood to be dialyzed into said fifth header passageway and out of said eighth header passageway, respectively, for flowing the blood through said multiple flow channels in both sides of the second plate in parallel flow relationship adjacent to the opposite surface of each of said membranes from the dialysate for dialyzing the blood, and the flow channels in said second plate having a depth of about 0.01 of an inch in the direction perpendicular to said membrane and having a large widthto depth ratio facing said membrane for exposing multiple thin wise films of flowing blood to the membranes for providing efficient exposure of the flowing blood to the surfaces of the membranes.

* * * * *